(12) United States Patent
Takahashi et al.

(10) Patent No.: US 6,180,568 B1
(45) Date of Patent: Jan. 30, 2001

(54) 4-ARYL-4-SUBSTITUTED PYRAZOLIDINE-3, 5-DIONE DERIVATIVES

(75) Inventors: Nobuyoshi Takahashi; Hirofumi Nakagawa; Yoshinori Endo, all of Naruto (JP)

(73) Assignee: Otsuka Kagaku Kabushiki Kaisha, Osaka (JP)

( * ) Notice: Under 35 U.S.C. 154(b), the term of this patent shall be extended for 0 days.

(21) Appl. No.: 09/509,821

(22) PCT Filed: Oct. 7, 1998

(86) PCT No.: PCT/JP98/04525

§ 371 Date: Apr. 19, 2000

§ 102(e) Date: Apr. 19, 2000

(87) PCT Pub. No.: WO99/20610

PCT Pub. Date: Apr. 29, 1999

Related U.S. Application Data

(63) Continuation of application No. PCT/JP98/04525, filed on Oct. 7, 1998.

(30) Foreign Application Priority Data

Oct. 21, 1997 (JP) .................................................. 9/307933

(51) Int. Cl.[7] ........................... A01N 43/56; C07D 231/04
(52) U.S. Cl. ....................................... 504/282; 548/366.4
(58) Field of Search ........................... 504/282; 548/366.4

(56) References Cited

U.S. PATENT DOCUMENTS 5,332,720  7/1994  Kruger et al. .
5,494,890  2/1996  Cederbaum et al. .
5,747,516  5/1998  Brown et al. .

OTHER PUBLICATIONS

Abstract of Japanese Patent Publ. No. 08269015 dated Oct. 15, 1996.

Primary Examiner—Robert W. Ramsuer
Assistant Examiner—Sonya N. Wright
(74) Attorney, Agent, or Firm—Arent Fox Kintner Plotkin & Kahn, PLLC

(57) ABSTRACT

A 4-aryl-4-substituted pyrazolidine-3,5-dione derivative represented by the formula (1) is useful as an effective component of a miticide, insecticide or herbicide

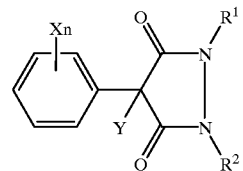

(1)

wherein $R^1$ and $R^2$ are each independently alkyl group having 1 to 4 carbon atoms, or $R^1$ and $R^2$, when taken together, represent saturated or unsaturated bivalent hydrocarbon group having 3 or 4 carbon atoms which may optionally be substituted with alkyl group having 1 to 4 carbon atoms, or halogen atom, X is alkyl group having 1 to 4 carbon atoms, haloalkyl group having 1 to 4 carbon atoms or halogen atom, Y is halogen atom or nitro group, and n is an integer of 0 to 3.

6 Claims, No Drawings

4-ARYL-4-SUBSTITUTED PYRAZOLIDINE-3,5-DIONE DERIVATIVES

This application is a 371 of PCT/Jp98/04525 filed Oct. 7, 1998.

TECHNICAL FIELD

The present invention relates to novel 4-aryl-4-substituted pyrazolidine-3,5-dione derivatives and to a miticide, an insecticide or a herbicide each containing the derivative as their active component.

BACKGROUND ART

Heretofore some kinds of 4-aryl-4-halopyrazolidine-3,5-dione derivatives have been known. For example, An. Quim. vol. 71, 396 to 399 (1975) discloses that compounds A, B and C to be described later, i.e. 4-aryl-4-halopyrazolidine-3,5-dione derivatives, can be prepared by Diels-Alder reaction between 4-chloro-4-phenylpyrazoline-3,5-dione and diene. Further An. Quim. vol. 75, 931 to 935 (1979) describes the under-mentioned compounds D and E as an intermediate for preparing 13,14-azasteroid, the compounds being prepared by Diels-Alder reaction between 4-chloro-4-phenylpyrazoline-3,5-dione and diene. In addition, Comment., Pontif. Acad. Sci. vol.2, 8 (1975) sets forth that compounds A, B and C to be described later can be prepared by chlorination of the corresponding 4-phenylpyrazolidine-3,5-dione derivative.

However, the compounds of the invention represented by the formula (1) are novel compounds which are not included in conventional compounds.

On the other hand, 4-aryl-4-nitropyrazolidine-3,5-dione derivatives are entirely novel compounds.

Compound A

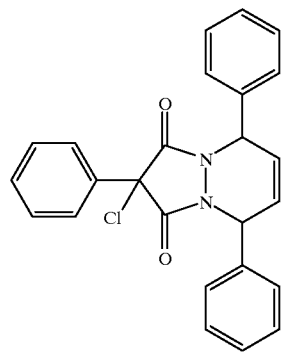

Compound B

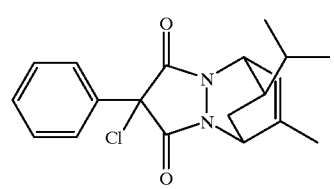

Compound C

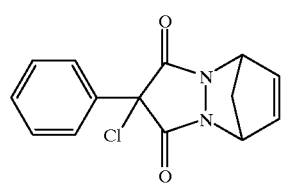

Compound D

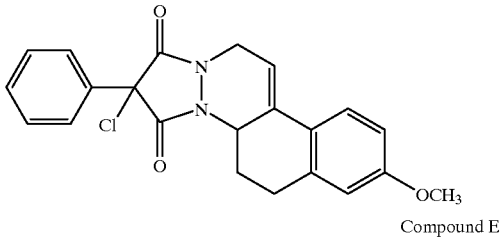

Compound E

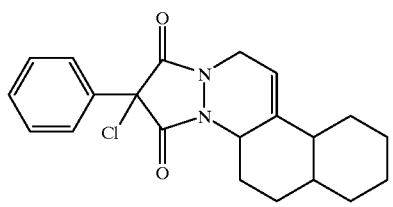

With insecticides and miticides in use for many years, pest insects have acquired resistance in recent years and become difficult to control with conventional insecticides. Accordingly it is expected to develop novel insecticides. Also in the herbicide field, the development of novel herbicides are expected.

An object of the present invention is to provide 4-aryl-4-substituted pyrazolidine-3,5-dione derivatives which have not only extremely high insecticidal and miticidal activities but a high herbicidal activity.

DISCLOSURE OF THE INVENTION

The present invention provides a 4-aryl-4-substituted pyrazolidine-3,5-dione derivative represented by the formula (1), a process for preparing the same and a miticide, an insecticide or a herbicide each containing the derivative

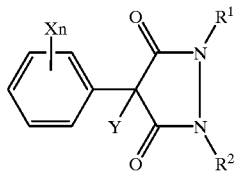

(1)

wherein $R^1$ and $R^2$ are each independently alkyl group having 1 to 4 carbon atoms, or $R^1$ and $R^2$, when taken together, represent saturated or unsaturated bivalent hydrocarbon group having 3 or 4 carbon atoms which may optionally be substituted with alkyl group having 1 to 4 carbon atoms or halogen atom, X is alkyl group having 1 to 4 carbon atoms, haloalkyl group having 1 to 4 carbon atoms or halogen atom, Y is halogen atom or nitro group, and n is an integer of 0 to 3.

Examples of alkyl groups having 1 to 4 carbon atoms in the formula (1) are methyl, ethyl, n-propyl, isopropyl, n-butyl, isobutyl, sec-butyl and tert-butyl.

Examples of haloalkyl groups having 1 to 4 carbon atoms are fluoromethyl, chloromethyl, bromomethyl, iodomethyl, difluoromethyl, trifluoromethyl, 2-fluoroethyl, 2-chloroethyl, 1-fluoroethyl, pentafluoroethyl, 1-fluoropropyl, 2-chloropropyl, 3-fluoropropyl, 3-chloropropyl, 1-fluorobutyl, 1-chlorobutyl and 4-fluorobutyl.

Halogen atoms include fluorine, chlorine, bromine and iodine atoms.

Saturated or unsaturated divalent hydrocarbon groups having 3 or 4 carbon atoms include trimethylene, tetramethylene and propenylene groups.

The compounds of the present invention exhibit a high effect against various harmful organisms even when used at a low dose. These harmful organisms include, for example, the following agricultural harmful insects:

those of the order Tetranychus, e.g. spider mites such as *Tetranychus urticae, Panonychus citri, Panonychus ulmi, Tetranychus kanzawai*, etc. and Tarsonemidae such as *Polyphagotarsonemus latus;* those of the order Hemiptera, e.g. planthoppers such as *Laodelphax striatellus* and *Nilaparvata lugens*, leafhoppers such as *Nephotettix cincticeps* and *Arboridia apicalis*, aphides such as *Myzus persicae, Aphis gossyii* and *Ovatus malicolens*, shield-bugs, scales and whiteflies;

those of the order Thysanoptera such as *Scirtothrips dorsalis, Thrips palmi, Frankliniella occidentalis* and *Frankliniella intonsa;* and those of the order Diptera such as *Phytobia cepae HERING* and *Liriomyza trifolii.*

The compounds of the present invention have an activity against sanitary insect pests such as *Culex pipiens pallens, Musca domestica* and other insect pests as well as against agricultural harmful insects.

At a low dose, the compounds of the present invention can control weeds such as chickweed, Digitaria adscendens, *Monochoria vaginalis var. plantaginea, Echinochloa Crusgalli, Cyperus microiria Steud.* and *Cyperus serotinus Rottb.* which pose agricultural problems. The effectiveness of the compounds is specifically demonstrated in Test Examples on organisms to be described later.

Among the compounds of the present invention represented by the formula (1), a compound of the present invention represented by the formula (3) can be prepared according to the following reaction scheme

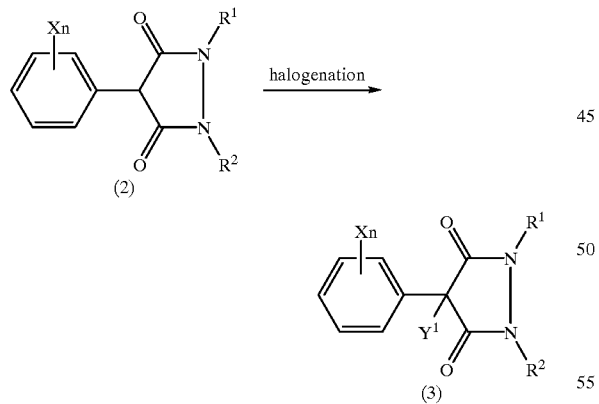

wherein $R^1$, $R^2$, X and n are as defined above and $Y^1$ is halogen atom.

According to the reaction scheme illustrated above, 4-arylpyrazolidine-3,5-dione derivative represented by the formula (2) is reacted with a halogenating agent in an inert solvent to give a compound of the invention represented by the formula (3).

The 4-arylpyrazolidine-3,5-dione derivative of the formula (2) can be prepared according to the method disclosed in JP-(PCT)-6-506201.

Examples of the halogenating agent used in halogenation are inorganic halides such as chlorine, thionyl chloride, sulfuryl chloride, phosgene, phosphorus trichloride, phosphorus pentachloride, bromine, thionyl bromide, sulfuryl bromide, phosphorus pentabromide and phosphorus oxybromide, organic halides such as N-chlorosuccinic acid imide (NCS) and N-bromosuccinic acid imide (NBS), alkali metal salts of hypochloric acid such as sodium hypochlorite, organic hypochlorine oxides such as tert-butyl hypochlorite. The amount of the halogenating agent used in the reaction is 1 to 10 equivalents, preferably 1 to 4 equivalents, per equivalent of the 4-arylpyrazolidine-3,5-dione derivative of the formula (2).

Examples of the solvent used in halogenation are halogenated hydrocarbons such as methylene chloride, 1,2-dichloroethane and carbon tetrachloride; aromatic hydrocarbons such as benzene, toluene, xylene and o-chlorobenzene; and ethers such as diethyl ether, tetrahydrofuran and 1,4-dioxane. The reaction temperature, although not specifically limited, is in the range of usually $-30°$ C. to the boiling point of the solvent used. It is possible to carry out the reaction at a temperature in the range of from $0°$ C. to the reflux temperature of the halogenating agent without use of the solvent. Although variable depending on the above-mentioned concentration, temperature and other factors, the reaction time is in the range of about 0.1 to about 6 hours. Optionally the reaction may be conducted in the presence of a catalyst. Examples of useful catalysts are benzoyl peroxide (BPO), 2,2'-azobisisobutyronitrile (AIBN), 4,4'-azobis-4-cyanovaleric acid (ACVA) and like radical initiators. The amount of the catalyst used is 0.00001 to 1 equivalent, preferably 0.0001 to 0.1 equivalent, per equivalent of the compound of the formula (3).

The 4-aryl-4-halopyrazolidine-3,5-dione derivative of the invention having the formula (3) can be purified by conventional methods such as solvent extraction, recrystallization and chromatographies such as column chromatography and preparative thin layer chromatography.

Among the compounds of the invention represented by the formula (1), a compound of the invention represented by the formula (4) can be prepared according to the following reaction scheme

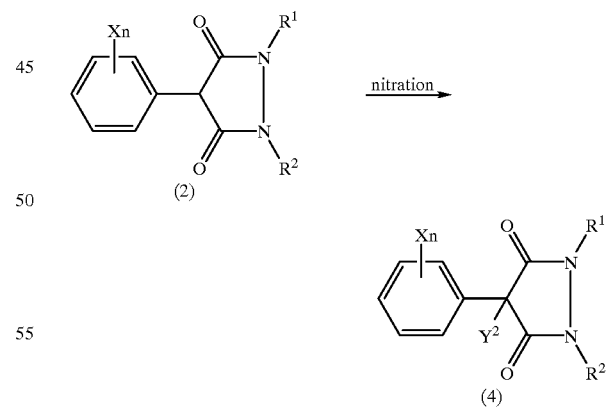

wherein $R^1$, $R^2$, X and n are as defined above and $y^2$ is nitro group.

According to the reaction scheme illustrated above, 4-arylpyrazolidine-3,5-dione derivative of the formula (2) is reacted with a nitrating agent in a solvent to give a compound of the invention represented by the formula (4).

Examples of the nitrating agent used herein are mixed acids, nitric acid, fuming nitric acid, and alkali metal salts of nitric acid such as potassium nitrate. The amount of the nitrating agent used in the reaction is 1 to 10 equivalents, preferably 1 to 2 equivalents, per equivalent of the 4-arylpyrazolidine-3,5-dione derivative of the formula (2). Examples of the solvent used in nitration include not only concentrated sulfuric acid useful as a component of mixed acids but also halogenated hydrocarbons such as methylene chloride and 1,2-dichloroethane, and acid anhydrides such as acetic anhydride. The reaction temperature, although not specifically limited, is in the range of 0° C. to the boiling point of the solvent used. Although variable depending on the above-mentioned concentration, temperature and other factors, the reaction time is usually in the range of about 0.1 to about 6 hours.

The 4-aryl-4-nitropyrazolidine-3,5-dione derivative of the formula (4) can be purified by conventional methods such as solvent extraction, recrystallization and chromatographies such as column chromatography and preparative thin layer chromatography.

Although the compound of the invention is usable as it is when used as an active component for an insecticide, a miticide or a herbicide, the compound of the invention is usually used as mixed with a solid carrier, liquid carrier or gas carrier, optionally together with a surfactant and other adjuvants useful for such formulations. The compound of the invention is provided in the form of oil formulation, emulsifiable concentrate, wettable powder, flowables, granules, dusts, aerosols or fumigants.

The compound of the invention is used in an amount of 0.01 to 95% by weight as contained in these formulations as their active component.

Examples of solid carriers useful in preparing the formulations are clays including kaolin clay, diatomite, water-containing synthetic silicon oxide, bentonite, Fubasami clay, and acid clay; talcs; ceramics; inorganic minerals such as Celite, quartz, sulfur, active carbon, calcium carbonate and hydrated silica; and chemical fertilizers such as ammonium sulfate, ammonium phosphate, ammonium nitrate, urea and ammonium chloride, these solid carriers being finely divided or granular. Examples of useful liquid carriers are water, alcohols such as methanol and ethanol, ketones such as acetone and methyl ethyl ketone, aromatic hydrocarbons such as benzene, toluene, xylene, ethylbenzene and methylnaphthalene, aliphatic hydrocarbons such as hexane, cyclohexane, kerosene and light oil, esters such as ethyl acetate and butyl acetate, nitriles such as acetonitrile and isobutyronitrile, ethers such as diisopropyl and dioxane, acid amides such as N,N-dimethylformamide and N,N-dimethylacetamide, halogenated hydrocarbons such as dichloromethane, trichloroethane and carbon tetrachloride, dimethyl sulfoxide, and vegetable oils such as soybean oil and cotton-seed oil. Examples of gas carriers, i.e., those of propellants, are butane gas, LPG (liquefied natural gas), dimethyl ether and carbon dioxide gas.

Examples of surfactants are alkylsulfuric acid esters, alkylsulfonic acid salts, alkylarylsulfonic acid salts, alkyl aryl ethers and polyoxyethylene adducts thereof, polyethylene glycol ethers, polyhydric alcohol esters and sugar alcohol derivatives.

Examples of adjuvants for the formlations, such as binders and dispersants, are casein, gelatin, polysaccharides such as starch, gum arabic, cellulose derivatives and alginic acid, lignin derivatives, bentonite, sugars and water-soluble synthetic high-molecular-weight substances such as polyvinyl alcohol, polyvinyl pyrrolidone and polyacrylic acids. Examples of stabilizers are PAP (acid isopropyl phosphate), BHT (2,6-di-tert-butyl-4-methylphenol), BHA (mixture of 2-tert-butyl-4-methoxyphenol and 3-tert-butyl-4-methoxyphenol), vegetable oils, mineral oils, surfactants and fatty acids or esters thereof.

The formulation thus obtained can be used as it is or as diluted, for example, with water. The formulation is usable also as admixed with other insecticides, nematocides, acaricides, fungicides, herbicides, plant growth regulators, synergists, soil improvers, baits and the like, or is usable simultaneously with such agents without mixing.

When used as an agricultural insecticide, a miticide or a herbicide, the compound of the invention is preferably applied usually in an amount of 0.01 to 500 g/100 $m^2$. When an emulsifiable concentrate, wettable powder or flowables are used as diluted with water, the compound is applied usually at a concentration of 0.1 to 1000 ppm, preferably 1 to 500 ppm. The granular or dust can be applied as it is without dilution.

The amount or concentration of application, although exemplified above, can be suitably increased or reduced according to the type of preparation, time, place, method of application, kind of pest insects, kind of weeds and extent of harm suffered.

BEST MODE OF CARRYING OUT THE INVENTION

The present invention will be described in detail with reference to the following preparation examples, formulation examples and test examples to which the invention, however, is not limited. First, preparation examples are given for the compounds of the invention. In Tables, Me stands for methyl; Et for ethyl and iPr for isopropyl.

PREPARATION EXAMPLE 1

Preparation of 4-chloro-1,2-dimethyl-4-(2,4,6-trimethylphenyl)pyrazolidine-3,5-dione (compound 19 of the invention)

There was refluxed with heating a mixture of 0.50 g (2.0 mmols) of 1,2-dimethyl-4-(2,4,6-trimethylphenyl) pyrazolidine-3, 5-dione, 0.32 g (2.4 mmols) of N-chlorosuccinic acid imide, 19 mg (0.08 mmol) of benzoyl peroxide and 20 ml of carbon tetrachloride for 30 minutes. Water was added to the reaction mixture, followed by extraction with chloroform. The extract was washed with an aqueous solution of saturated sodium hydrogencarbonate and a saturated solution of sodium chloride and was dried over anhydrous magnesium sulfate. The solvent was distilled off under reduced pressure. Then the residue was washed with hexane, thereby obtaining 0.44 g (yield 78%) of 4-chloro-1,2-dimethyl-4-(2,4,6-trimethylphenyl) pyrazolidine-3,5-dione in the form of yellowish white crystals.

PREPARATION EXAMPLE 2

Preparation of 4-chloro-4-(2-chlorophenyl)-1,2-dimethylpyrazolidine-3,5-dione (compound 3 of the invention) A chloroform solution (5 ml) of 0.28 g (2.1 mmols) of sulfuryl chloride was added dropwise to a solution of 0.50 g (2.1 mmols) of 4-(2-chlorophenyl)-1,2-dimethylpyrazolidine-3, 5-dione in 10 ml of chloroform with ice cooling. The mixture was stirred with ice cooling for 30 minutes. The reaction mixture was washed successively with water, an aqueous solution of saturated sodium hydrogencarbonate and a saturated solution of sodium chloride and was dried over anhydrous magnesium sulfate. The solvent was distilled off under reduced pressure. Then the residue was washed with hexane, thereby obtaining 0.43 g (yield 74%) of 4-chloro-1,2-dimethyl-4-(2-chlorophenyl) pyrazolidine-3,5-dione in the form of yellowish white crystals.

PREPARATION EXAMPLE 3
Preparation of 4-bromo-4-(2-chlorophenyl)-1,2-dimethylpyrazoline-3,5-dione (compound 21 of the invention)

A chloroform solution (5 ml) of 0.33 g (2.1 mmols) of bromine was added dropwise to a solution of 0.50 g (2.1 mmols) of 1,2-dimethyl-4-(2-chlorophenyl)pyrazolidine-3,5-dione in 10 ml of chloroform with ice cooling. The obtained mixture was stirred with ice cooling for 30 minutes. The reaction mixture was washed successively with water, an aqueous solution of saturated sodium hydrogencarbonate and a saturated solution of sodium chloride and was dried over anhydrous magnesium sulfate. The solvent was distilled off under reduced pressure. Then the residue was washed with hexane, thereby obtaining 0.50 g (yield 75%) of 4-bromo-4-(2-chlorophenyl)-1,2-dimethylpyrazoline-3, 5-dione in the form of yellow crystals.

PREPARATION EXAMPLE 4
Preparation of 1,2-dimethyl-4-nitro-4-(2,4,6-trimethylphenyl)pyrazolidine-3,5-dione (compound 36 of the invention)

A quantity of 0.13 ml (3.1 mmols) of fuming nitric acid was added to a solution of 0.70 g (2.8 mmols) of 1,2-dimethyl-4-(2,4,6-trimethylphenyl)pyrazolidine-3,5-dione in 20 ml of chloroform at room temperature. The obtained mixture was stirred at room temperature for 15 minutes. The reaction mixture was washed with water and was dried over anhydrous magnesium sulfate. The solvent was distilled off under reduced pressure. Then the residue was purified by column chromatography (benzene:ethyl acetate=3:1) to give 0.53 g (yield 64%) of 1,2-dimethyl-4-nitro-4-(2,4,6-trimethylphenyl)pyrazolidine-3,5-dione in the form of yellowish white crystals.

Tables 1 to 6 show the compounds prepared by any of the processes described in the Preparation Examples given above and the physicochemical properties of the compounds.

TABLE 1

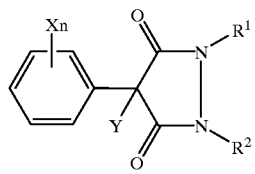

(1)

| Compound | Xn | Y | $R^1$ | $R^2$ | mp (° C.) |
|---|---|---|---|---|---|
| 1 | — | Cl | Me | Me | 93~94 |
| 2 | 2-F | Cl | Me | Me | 144~147 |
| 3 | 2-Cl | Cl | Me | Me | 192~193 |
| 4 | 2-Cl | Cl | Me | Et | 110~112 |
| 5 | 2-Cl | Cl | Me | iPr | 126~127 |
| 6 | 2-Cl | Cl | Et | Et | 129~130 |
| 7 | 3-Cl | Cl | Me | Me | 73~74 |
| 8 | 4-Cl | Cl | Me | Me | 178~179 |
| 9 | 2-Br | Cl | Me | Me | 197~198 |
| 10 | 2-Me | Cl | Me | Me | 168~169 |
| 11 | 2-$CF_3$ | Cl | Me | Me | 131~132 |
| 12 | 2,3-$Cl_2$ | Cl | Me | Me | 157~158 |
| 13 | 2,4-$Cl_2$ | Cl | Me | Me | 176~177 |
| 14 | 2,5-$Cl_2$ | Cl | Me | Me | 143~144 |

TABLE 1-continued

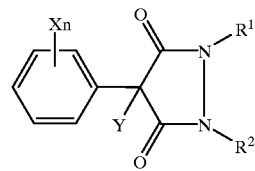

(1)

| Compound | Xn | Y | $R^1$ | $R^2$ | mp (° C.) |
|---|---|---|---|---|---|
| 15 | 2,6-$Cl_2$ | Cl | Me | Me | 147~148 |
| 16 | 3,4-$Cl_2$ | Cl | Me | Me | 120~121 |
| 17 | 3,5-$Cl_2$ | Cl | Me | Me | 127~128 |
| 18 | 2,4,6-$Cl_3$ | Cl | Me | Me | 185~186 |

TABLE 2

| Compound | Xn | Y | $R^1$ | $R^2$ | mp (° C.) |
|---|---|---|---|---|---|
| 19 | 2,4,6-$Me_3$ | Cl | Me | Me | 98~100 |
| 20 | — | Br | Me | Me | 100~101 |
| 21 | 2-Cl | Br | Me | Me | 198~199 |
| 22 | 2-Cl | Br | Et | Et | 143~144 |
| 23 | 4-Cl | Br | Me | Me | 185~186 |
| 24 | 2-Me | Br | Me | Me | 176~177 |
| 25 | 2,3-$Cl_2$ | Br | Me | Me | 178~179 |
| 26 | 2,4-$Cl_2$ | Br | Me | Me | 174~175 |
| 27 | 2,6-$Cl_2$ | Br | Me | Me | 138~139 |
| 28 | 2,5-$Cl_2$ | Br | Me | Me | 178~179 |
| 29 | 3,4-$Cl_2$ | Br | Me | Me | 124~125 |
| 30 | 3,5-$Cl_2$ | Br | Me | Me | 119~120 |
| 31 | 2,4,6-$Me_3$ | Br | Me | Me | 101~103 |
| 32 | 2-Cl | $NO_2$ | Me | Me | 118~119 |
| 33 | 2-Cl | $NO_2$ | Et | Et | 109~110 |
| 34 | 4-Cl | $NO_2$ | Me | Me | 123~124 |
| 35 | 2-Me | $NO_2$ | Me | Me | 106~107 |
| 36 | 2,3-$Cl_2$ | $NO_2$ | Me | Me | 130~131 |
| 37 | 2,4,6-$Me_3$ | $NO_2$ | Me | Me | 136~137 |

TABLE 3

| Compound | $^1$H-NMR δ(ppm, $CDCl_3$) |
|---|---|
| 1 | 3.33(s, 6H), 7.35(m, 3H), 7.62~7.70(m, 2H) |
| 2 | 3.36(s, 6H), 7.31(dd, 1H), 7.35~7.45(m, 1H), 7.50(dd, 1H), 7.87(dt, 1H) |
| 3 | 3.37(s, 6H), 7.32~7.47(m, 3H), 8.01(dd, 1H) |
| 4 | 1.32(t, 3H), 3.34(s, 3H), 3.58~3.70(m, 1H), 3.97~4.10(m, 1H), 7.35~7.45(m, 3H), 8.02(dd, 1H) |
| 5 | 1.47~1.68(m, 6H), 3.38(s, 3H), 4.34~4.50(m, 1H), 7.35~7.45(m, 3H), 8.00(dt, 1H) |
| 6 | 1.31(t, 6H), 3.70~3.95(m, 4H), 7.36~7.49(m, 3H), 8.02(d, 1H) |
| 7 | 3.34(s, 6H), 7.30~7.40(m, 2H), 7.60~7.65(m, 1H), 7.70(m, 1H) |
| 8 | 3.34(s, 6H), 7.39(d, 2H), 7.68(d, 2H), |
| 9 | 3.39(s, 6H), 7.31(dt, 1H), 7.49(dt, 1H), 7.57(dd, 1H), 8.04(dt, 1H) |
| 10 | 2.19(s, 3H), 3.38(s, 6H), 7.16(dd, 1H), 7.28~7.36(m, 2H), 7.86(dd, 1H) |
| 11 | 3.35(s, 6H), 7.58(t, 1H), 7.68~7.78(m, 2H), 8.31(d, 1H) |
| 12 | 3.38(s, 6H), 7.39(t, 1H), 7.56(dd, 1H), 7.96(dd, 1H) |
| 13 | 3.37(s, 6H), 7.38~7.45(m, 2H), 7.95(d, 1H) |
| 14 | 3.37(s, 6H), 7.31(d, 1H), 7.37(dd, 1H) 8.00(d, 1H) |
| 15 | 3.35(s, 6H), 7.23(d, 1H), 7.38(d, 2H) |
| 16 | 3.35(s, 6H), 7.49(d, 1H), 7.61(dd, 1H) 7.83(d, 1H) |
| 17 | 3.36(s, 6H), 7.40(d, 1H), 7.63(d, 2H) |
| 18 | 3.35(s, 6H), 7.41(s, 2H) |

TABLE 4

| Compound | ¹H-NMR δ(ppm, CDCl₃) |
|---|---|
| 19 | 2.23(s, 3H), 2.43(s, 6H), 3.35(s, 6H), 6.85(s, 2H) |
| 20 | 3.32(s, 6H), 7.32~7.42(m, 3H), 7.80~7.85(m, 2H) |
| 21 | 3.37(s, 6H), 7.30~7.40(m, 3H), 8.06(dd, 1H) |
| 22 | 1.31(t, 6H), 3.72~3.95(m, 4H), 7.32~7.45(m, 3H), 8.05~8.12(m, 1H) |
| 23 | 3.33(s, 6H), 7.37(d, 2H), 7.84(d, 2H) |
| 24 | 2.16(s, 3H), 3.37(s, 6H), 7.11~7.15(m, 1H), 7.27~7.36(m, 3H), 7.89~7.93(m, 1H) |
| 25 | 3.38(s, 6H), 7.36(t, 1H), 7.56(dd, 1H), 8.00(dd, 1H) |
| 26 | 3.36(s, 6H), 7.35~7.40(m, 2H), 7.99(d, 1H) |
| 27 | 3.35(s, 6H), 7.22(d, 1H), 7.78(d, 1H) |
| 28 | 3.37(s, 6H), 7.29(d, 1H), 7.35(dd, 1H), 8.05(d, 1H) |
| 29 | 3.33(s, 6H), 7.47(d, 1H), 7.78(dd, 1H), 8.00(d, 1H) |
| 30 | 3.34(s, 6H), 7.38(d, 1H), 7.80(d, 2H) |
| 31 | 2.23(s, 3H), 2.43(s, 6H), 3.34(s, 6H), 6.85(s, 2H) |
| 32 | 3.36(s, 6H), 7.26(d, 1H), 7.33~7.50(m, 3H) |
| 33 | 1.25(t, 6H), 3.70~3.90(m, 4H), 7.24(dd, 1H), 7.36(dt, 1H), 7.44(dt, 1H), 7.51(dd, 1H) |
| 34 | 3.38(s, 6H), 7.46(d, 2H), 7.87(d, 2H) |
| 35 | 2.48(s, 3H), 3.37(s, 6H), 7.12~7.40(m, 4H) |
| 36 | 3.40(s, 6H), 7.22(d, 1H), 7.36(dd, 2H), 7.52(d, 1H) |
| 37 | 2.25(s, 6H), 2.26(s, 3H), 3.39(s, 6H), 6.90(s, 2H) |

TABLE 5

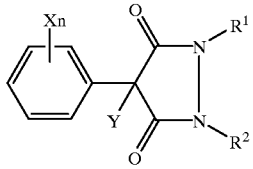

(1)

| Compound | Xn | Y | -R¹-R²- | mp (° C.) |
|---|---|---|---|---|
| 38 | 2-Cl | Cl | —(CH₂)₃— | 228~229 |
| 39a* | 2-Cl | Cl | —CH(Me)CH₂CH₂— | 209~210 |
| 39b* | 2-Cl | Cl | —CH(Me)CH₂CH₂— | 208~209 |
| 40 | 2-Cl | Cl | —(CH₂)₄— | 167~168 |
| 41 | 2-Cl | Cl | —CH(Me)CH₂CH₂CH₂— | 128~130 |
| 42 | 2-Cl | Cl | —CH=CHCH₂CH₂— | 135~137 |
| 43 | 2,4,6-Me₃ | Cl | —(CH₂)₄— | 132~133 |
| 44 | 2-Cl | NO₂ | —(CH₂)₄— | 148~149 |
| 45 | 2-Cl | Cl | —CHClCHClCH₂CH₂— | 148~149 |

(Note) Compound 39a is a compound wherein a diastereomer has a higher Rf value in thin layer chromatography on silica gel (25 TLC plastic sheets 20×20 cm, silica gel 60F₂₅₄, Merck/eluent: hexane/ethyl acetate=1/1), and Compound 39b is a compound wherein a diastereomer has a lower Rf value in said chromatography.

TABLE 6

| Compound | ¹H-NMR δ(ppm, CDCl₃) |
|---|---|
| 38 | 2.40~2.53(m, 2H), 3.60~3.74(m, 2H), 4.08~4.18(m, 2H), 7.36~7.48(m, 3H), 7.99(dd, 1H) |
| 39a | 1.52(d, 3H), 2.12~2.22(m, 1H), 2.52~2.66(m, 1H), 3.69~3.79(m, 1H), 4.00~4.08(m, 1H) 4.37~4.48(m, 1H), 7.33~7.47(m, 3H), 7.98(dd, 1H) |
| 39b | 1.62(d, 3H), 2.16~2.27(m, 1H), 2.64~2.75(m, 1H), 3.74~3.85(m, 1H), 3.90~4.00(m, 1H) 4.25~4.38(m, 1H), 7.35~7.45(m, 3H), 8.08(dd, 1H) |
| 40 | 1.80~1.95(m, 4H), 3.65~3.80(m, 4H), 7.35~7.48(m, 3H), 8.02(dd, 1H) |
| 41 | 1.35~1.48(m, 3H), 1.70~2.10(m, 4H), |

TABLE 6-continued

| Compound | ¹H-NMR δ(ppm, CDCl₃) |
|---|---|
| | 3.12~3.46(m, 1H), 4.12~4.27(m, 1H), 4.42~4.65(m, 1H), 7.35~7.45(m, 3H), 8.01(d, 1H) |
| 42 | 2.40~2.67(m, 2H), 3.69(ddd, 1H), 4.25(ddd, 1H), 5.37~5.44(m, 1H), 7.15(d, 1H), 7.35~7.50(m, 3H) 8.03(d, 1H) |
| 43 | 1.80~1.95(m, 4H), 2.23(s, 3H), 2.44(s, 6H), 3.65~3.77(m, 4H), 8.65(s, 2H) |
| 44 | 1.78~2.00(m, 4H), 3.65~3.85(m, 4H), 7.27~7.50(m, 4H) |
| 45 | 2.18(brd, 1H), 2.8~2.94(m, 1H), 3.75(ddd, 1H), 4.38(ddd, 1H), 4.56(dd, 1H), 6.37(s, 1H), 7.37~7.50(m, 3H), 7.95~8.0(m, 1H) |

Formulation Examples are given below wherein the parts are by weight.

FORMULATION EXAMPLE 1
(Emulsifiable concentrate)

Ten parts of each compound of the invention was dissolved in 45 parts of Solvesso 150 and 35 parts of N-Methylpyrrolidone. Ten parts of Sorpol 3005X (emulsifier manufactured by Toho Kagaku Co., Ltd.) was added. These ingredients were mixed together with stirring to give a 10% emulsifiable concentrate.

FORMUALTION EXAMPLE 2
(Wettable powder)

Twenty parts of each compound of the invention was added to a mixture of 2 parts of sodium lauryl sulfate, 4 parts of sodium lignin sulfonate, 20 parts of finely divided water-containing synthetic silicon oxide and 54 parts of clay. These ingredients were mixed together with stirring by a juice mixer to give a 20% wettable powder.

FORMUALTION EXAMPLE 3
(Granules)

Each compound of the invention (5 parts) was mixed with 2 parts of sodium dodecylbenzene sulfonate, 10 parts of bentonite and 83 parts of clay, followed by thorough agitation. A suitable amount of water was added to the mixture and further stirred. The mixture was granulated by a granulator and air-dried to give 5% granules.

FORMULATION EXMAPLE 4
(Dust)

Each compound of the invention (1 part) was dissolved in a suitable amount of acetone. To the solution were added 5 parts of finely divided water-containing synthetic silicon oxide, 0.3 part of acid isopropyl phosphate (PAP) and 93.7 parts of clay. The ingredients were mixed together with stirring by a juice mixer and the acetone was removed by evaporation to give a 1% dust formulation.

FORMUALTION EXAMPLE 5
(Flowables)

Each compound of the invention (20 parts) was mixed with 20 parts of water containing 3 parts of polyoxyethylene tristyrylphenyl ether phosphoric acid ester triethanolamine and 0.2 part of Roadazyl 426 R (silicon-type deforming agent). The mixture was pulverized by wet method using a dynomill. Thereafter the mixture was mixed with 60 part of water containing 8 parts of propylene glycol and 0.32 part of xanthane gum to give a 20% suspension in water.

Test Examples are given below to show that the compounds of the invention are useful as an active agent for a miticide, insecticide and herbicide.

TEST EXAMPLE 1
Insecticidal Test on *Tetranychus uricae*

Leaves of kidney bean plants (about 3.5×4.5 cm) were placed on non-woven fabric pieces (4.5×5.5 cm) containing sufficient water. Then, about 30 female adult insects of *Tetranychus uricae* were released on the leaves to stay on the leaves, which were then placed in a thermostatic chamber at a temperature of 25±2° C. and a humidity of 40%. An insecticidal formulation (200 ppm) was prepared by adding an aqueous solution (100 ppm) of Sorpol 355 (product of Toho Kagaku Co., Ltd.) to a methanol solution of a compound of the invention. Subsequently the formulation (2.0 ml) was sprayed over the leaves, and was air-dried. The leaves were left to stand in the thermostatic chamber (25±2° C., humidity 50%) for 2 days. Then a mortality of Tetranychus uricae was checked.

A mortality of more than 50% is ascribed to the following compounds of the invention: Compounds 3, 5, 9, 10 13, 14, 15, 18, 19, 21, 24, 26, 27, 28, 31, 35, 37, 38, 39a, 39b, 41 and 43.

TEST EXAMPEL 2
Insecticidal Test on *Myzus persicae*

Leaves of cabbage plants in 2-leaf stage (2 cm in diameter) were placed on non-woven fabric pieces containing sufficient water. About 30 larvae of *Myzus persicae* were released on the leaves to stay on the leaves, which were then placed in a thermostatic chamber (25±2° C., humidity 50%). Next day, the insecticidal formulation (200 ppm) described in Test Example 1 was sprayed over the leaves and was air-dried. The leaves were left to stand in the thermostatic chamber for 3 days. Then a mortality of *Myzus persicae* was assessed.

A mortality of more than 50% is ascribed to the following compounds of the invention:

Compounds 15, 18, 19, 31, 37 and 43.

TEST EXAMPLE 3
Insecticidal Test on *Laodelphax striatellus*

2.5 ml of the insecticidal formulation (conc. 200 ppm) described in Test Example 1 was applied dropwise to the surface of soil in pots (3×4×4 cm) having planted therein paddy rice seedlings. After the formulation was permeated into the soil, 30 third instar larvae of *Laodelphax striatellus* were released into the pots. Then the pots were left to stand in a thermostatic chamber (25±2° C., humidity 50%). After 7 days, a mortality of Laodelphax striatellus was checked.

A mortality of more than 50% is ascribed to the following compounds of the invention:

Compounds 3, 4, 5, 9, 10, 13, 15, 18, 19, 21, 26, 27, 31, 32, 37 and 43.

TEST EXAMPLE 4
Test for Herbicidal Activity (soil treatment test and stem- and leaf-treatment test)

A specified amount of the compound of the invention was dissolved in a small amount of acetone. Then the solution was diluted with an aqueous solution of Tween 80 to give a herbicidal formulation (2000 ppm). Pots (square, 5 cm in each side) were filled with paddy soil and a suitable quantity of seeds of chickweed, Aeschynomene indica, Echinochloa Crus-galli and Digitaria adscendens were sown in the pots. The pots were then covered with a thin layer of soil. In the soil treatment, the herbicidal formulation was uniformly applied dropwise over the soil surface immediately after sowing the seeds. In the stem- and leaf-treatment, the herbicidal formulation was sprayed over the soil after 8-day growth of the plants at room temperature of 23° C. in a 16-hour lighting chamber. The herbicidal formulation was applied in an amount of 4 kg/ha calculated as the active component and was used in an amount of 0.5 ml both in the soil treatment and in the stem- and leaf-treatment. The pots for soil treatment was accommodated in a chamber maintained at 23° C. The pots for stem- and leaf-treatment were transferred to the glass green house. After 14-day growth under this condition, the herbicidal activity was evaluated according to 6-grade criteria; 0 (inactivity), 10, 20, 30, 40 and 50 (complete withering). The results are shown in Tables 7 and 8.

TABLE 7

| | | soil treatment | | | |
|---|---|---|---|---|---|
| Cmpd. | amount (kg/ha) | chick-weed | *aeschynomene indica* | *digitaria* | *Echinochloa Crus-galli* |
| 19 | 4 | 50 | 30 | 50 | 50 |
| 27 | 4 | 50 | 10 | 50 | 50 |
| 31 | 4 | 50 | 40 | 50 | 50 |

TABLE 8

| | | stem-and leaf-treatment | | | |
|---|---|---|---|---|---|
| Cmpd. | amount (kg/ha) | chick-weed | *Aeschynomene indica* | *digitaria* | *Echinochloa Crus-galli* |
| 19 | 4 | 40 | 10 | 40 | 50 |
| 27 | 4 | 30 | 10 | 40 | 50 |
| 31 | 4 | 50 | 40 | 50 | 50 |

TEST EXAMPLE 5
Test for herbicidal activity (treatment under submerged condition)

Pots (8 cm in diameter) were filled with paddy soil. Water was poured into the pots to create a submerged condition. Next day, seeds of Echinochloa Crus-galli, Cyperus microiria Steud. and Monochoria vaginalis var. plantaginea were sown and the roots of Cyperus serotinus Rottb. were buried in the soil, followed by treatment with the herbicidal formulation prepared in Test Example 4. One ml of the herbicidal formulation was applied dropwise to the surface of water in the pots under submerged condition. The specified amount of the herbicidal formulation is 4 kg/ha calculated as the active component. After 14-day growth of plants in the glass green house following the treatment, the herbicidal activity was evaluated according to 6-grade criteria; 0 (inactivity), 10, 20, 30, 40 and 50 (complete withering). The results are shown in Table 9.

TABLE 9

| | | treatment under submerged condition | | | |
|---|---|---|---|---|---|
| Cmpd. | amount (kg/ha) | *Monochoria vaginalis* var. *plantaginea* | *Cyperus microiria* Steud. | *Echinochloa Crus-galli* | *Cyperus serotinus* Rottb. |
| 19 | 4 | 50 | 50 | 50 | 50 |
| 27 | 4 | 20 | 0 | 50 | 50 |
| 31 | 4 | 50 | 50 | 50 | 50 |

INDUSTRIAL APPLICABILITY

The compounds of the invention show high insecticidal and miticidal activities against many species of agricultural insect pests. Further, the compounds of the invention exhibit a high herbicidal activity against many species of weeds which would pose agricultural problems. Therefore, the compounds of the invention can provide useful formulations for control of harmful organisms.

What is claimed is:

1. A 4-aryl-4-substituted pyrazolidine-3,5-dione derivative represented by the formula (1)

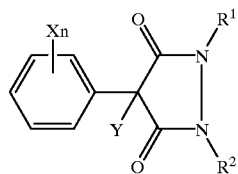

(1)

wherein $R^1$ and $R^2$ are each independently alkyl group having 1 to 4 carbon atoms, or $R^1$ and $R^2$, when taken together, represent saturated or unsaturated bivalent hydrocarbon group having 3 or 4 carbon atoms which may optionally be substituted with alkyl group having 1 to 4 carbon atoms, or halogen atom, X is alkyl group having 1 to 4 carbon atoms, haloalkyl group having 1 to 4 carbon atoms or halogen atom, Y is halogen atom or nitro group, and n is an integer of 0 to 3.

2. A 4-aryl-4-halopyrazolidine-3,5-dione derivative as defined in claim 1 wherein Y in the formula (1) is halogen atom.

3. A 4-aryl-4-nitropyrazolidine-3,5-dione derivative as defined in claim 1 wherein Y in the formula (1) is nitro group.

4. A process for preparing 4-aryl-4-halopyrazolidine-3,5-dione derivative comprising halogenating 4-aryl-pyrazolidine-3,5-dione derivative of the formula (2) to obtain 4-aryl-4-halopyrazolidine-3,5-dione derivative of the formula (3)

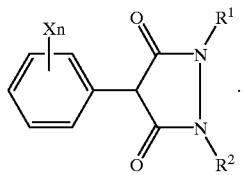

(2)

wherein $R^1$, $R^2$, X and n are as defined above

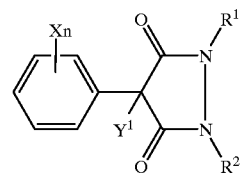

(3)

wherein $R^1$, $R^2$, X and n are as defined above, $Y^1$ is halogen atom.

5. A process for preparing 4-aryl-4-nitropyrazolidine-3,5-dione derivative comprising halogenating 4-aryl-pyrazolidine-3,5-dione derivative of the formula (2) to obtain 4-aryl-4-nitropyrazolidine-3,5-dione derivative of the formula (4)

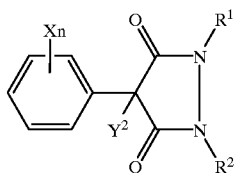

(4)

wherein $R^1$, $R^2$, X and n are as defined above, $y^2$ is nitro group.

6. A miticide, insecticide or herbicide comprising as an effective component at least one of 4-aryl-4-substituted pyrazolidine-3,5-dione derivative of claim 1.

* * * * *